United States Patent [19]

Hirschfeld

[11] Patent Number: 4,799,756
[45] Date of Patent: * Jan. 24, 1989

[54] REMOTE MULTI-POSITION INFORMATION GATHERING SYSTEM AND METHOD

[75] Inventor: Tomas B. Hirschfeld, Livermore, Calif.

[73] Assignee: The Regents of the University of California, Berkeley, Calif.

[*] Notice: The portion of the term of this patent subsequent to Dec. 2, 2003 has been disclaimed.

[21] Appl. No.: 793,961

[22] Filed: Nov. 1, 1985

Related U.S. Application Data

[60] Division of Ser. No. 480,844, Mar. 31, 1983, Pat. No. 4,626,693, which is a continuation of Ser. No. 194,684, Oct. 6, 1980, abandoned.

[51] Int. Cl.⁴ .............................................. G02B 6/32
[52] U.S. Cl. .............................. 350/96.18; 350/96.10; 250/458.1; 250/461.1; 250/461.2
[58] Field of Search ............... 350/96.10, 96.15, 96.16, 350/96.18, 96.19, 96.20, 96.29, 96.30; 250/458.1, 227, 231 R, 231 P, 354.1, 461.1, 461.2; 356/32, 44, 317, 318; 128/634

[56] References Cited

U.S. PATENT DOCUMENTS

| | | | |
|---|---|---|---|
| 3,591,810 | 7/1971 | Jackson | 250/83 |
| 3,656,832 | 4/1972 | Judin | 350/96.18 |
| 3,875,422 | 4/1975 | Stolen | 350/96.18 |
| 3,904,373 | 9/1975 | Harper | 23/253 TP |
| 4,003,707 | 1/1977 | Lübbers | 23/232 R |
| 4,021,099 | 5/1977 | Kawasaki et al. | 350/96.18 |
| 4,075,493 | 2/1978 | Wickersheim | 250/461 R |
| 4,136,566 | 1/1979 | Christensen | 73/356 |
| 4,154,529 | 5/1979 | Dyott | 350/96.18 |
| 4,158,310 | 6/1979 | Ho | 73/705 |
| 4,179,927 | 12/1979 | Saaski | 73/350 |
| 4,200,110 | 4/1980 | Peterson | 128/634 |
| 4,215,940 | 8/1980 | Lübbers | 356/402 |
| 4,255,053 | 3/1981 | Lübbers | 356/318 |
| 4,257,672 | 3/1981 | Balliet | 350/96.17 |
| 4,269,516 | 5/1981 | Lübbers | 356/427 |
| 4,270,050 | 6/1981 | Brogardh | 250/231 R |
| 4,272,484 | 6/1981 | Lübbers | 422/68 |
| 4,272,485 | 6/1981 | Lübbers | 422/68 |
| 4,273,442 | 6/1981 | Lübbers | 356/326 |
| 4,281,245 | 7/1981 | Brogardh | 250/227 |
| 4,290,667 | 9/1981 | Chown | 350/96.18 |
| 4,296,318 | 10/1981 | Mezzetti | 250/225 |
| 4,300,811 | 11/1981 | Ettenberg et al. | 350/96.15 |
| 4,306,877 | 12/1981 | Lübbers | 23/230 R |
| 4,344,438 | 8/1982 | Schultz | 128/634 |
| 4,425,907 | 1/1984 | Younghouse | 350/96.10 |
| 4,626,693 | 12/1986 | Hirschfeld | 250/458.1 |

OTHER PUBLICATIONS

Haaijman, "A New Standard for Fluorescein and Rhodamine Emission Measurement", *Journal of Immunological Methods*, Oct. 1974, pp. 359–374.

Primary Examiner—William L. Sikes
Assistant Examiner—Frank González
Attorney, Agent, or Firm—Flehr, Hohbach, Test, Albritton & Herbert

[57] ABSTRACT

A technique for gathering specific information from various remote locations, especially fluorimetric information characteristic of particular materials at the various locations is disclosed herein. This technique uses a single source of light disposed at still a different, central location and an overall optical network including an arrangement of optical fibers cooperating with the light source for directing individual light beams into the different information bearing locations. The incoming light beams result in corresponding displays of light, e.g., fluorescent light, containing the information to be obtained. The optical network cooperates with these light displays at the various locations for directing outgoing light beams containing the same information as their cooperating displays from these locations to the central location. Each of these outgoing beams is applied to a detection arrangement, e.g., a fluorescence spectroscope, for retrieving the information contained thereby.

22 Claims, 3 Drawing Sheets

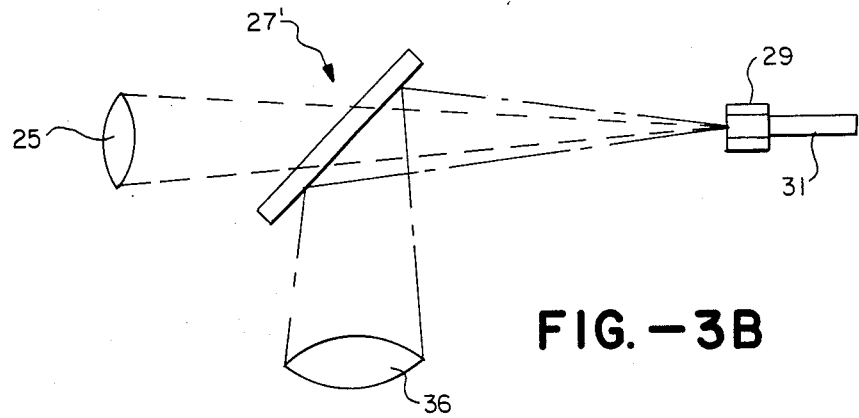
FIG.—3B
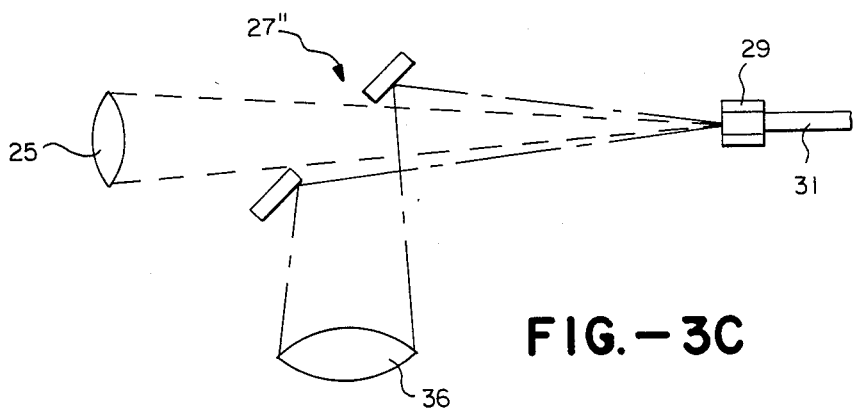
FIG.—3C
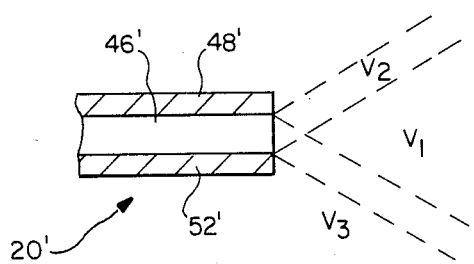
FIG.—4A
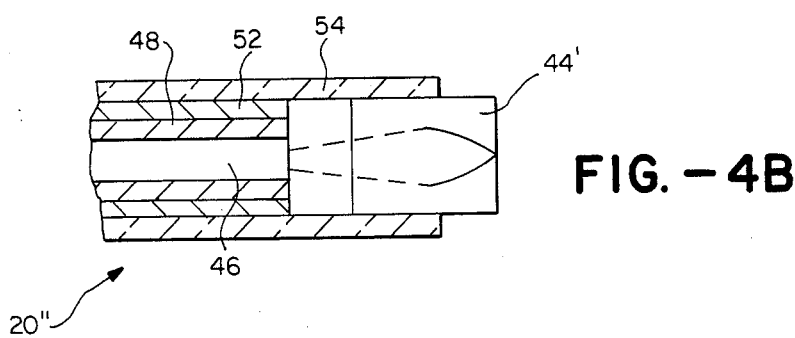
FIG.—4B

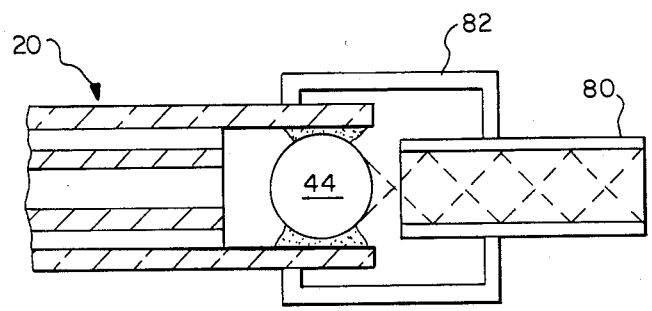
FIG.—4C
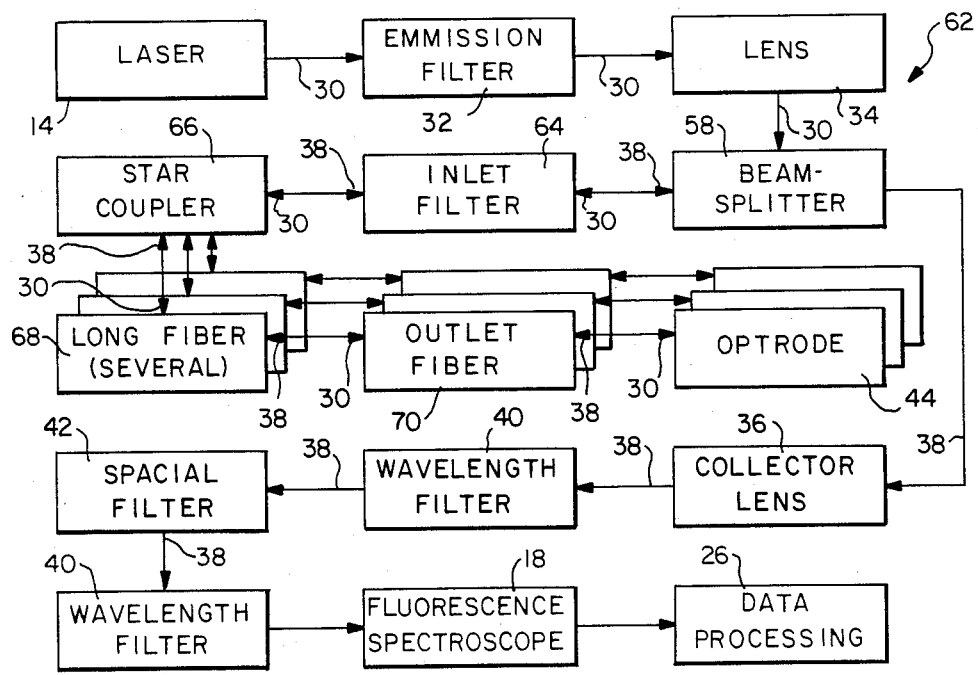
FIG.—5

REMOTE MULTI-POSITION INFORMATION GATHERING SYSTEM AND METHOD

The Government has rights in this invention pursuant to Contract No. W-7405 ENG. 48 awarded by the U.S. Dept. of Energy.

This is a division of application Ser. No. 480,844, now U.S. Pat. No. 4,626,693 filed 3-31-83 which is a continuation of U.S. Ser. No. 194,684 filed 10-6-80 now abandoned.

The present invention relates generally to techniques for gathering or obtaining information at one or more remote locations and more particularly to a specific technique for obtaining from one or more remote locations fluorimetric information, that is, fluorescent light emanating from and characteristic of particular materials at these locations, without utilizing entirely separate information gathering apparatus located at each of the information bearing locations.

Modern technology is dependent on analytical monitoring and control as well as information gathering processes. However, in many cases, the analysis or information gathering process must be done from a distance, for example, where the data or information is located at an underground nuclear waste-disposal site, inside a nuclear reactor, at the working zone of a coal-liquefication reactor, or like environments which are much too hostile for most in situ analytical devices. In this regard, it should be noted that the problem is not limited to industry. In the field of research and development the disadvantages of putting an expensive analytical instrument into an extremely hostile environment such as a highly radioactive hot cell, or the like must be weighed against the need for the information to be obtained thereby.

Heretofore, the various problems just described resulted in the development of especially ruggedized but extremely expensive instruments or, when possible, of equally rugged and expensive sampling systems capable of collecting representative samples for delivery to the instrument, without alteration. This is especially impractical when a large number of these instruments or sampling systems are required when monitoring and/or information gathering is to take place at about the same time at a number of remote locations.

SUMMARY OF THE INVENTION

In view of the foregoing, one object of the present invention is to provide an uncomplicated, reliable and yet economical technique for obtaining specific information from remote locations, especially hostile locations or at substantial distances (e.g. 1000 feet) where required and without requiring ruggedized instruments or equally rugged sampling systems at the measurement site.

A more particular object of the present invention is to provide a multi-location information gathering technique of the type just recited in which the primary instrumentation is common to all of the information bearing locations and all of these locations are interrogated substantially simultaneously.

Another particular object of the present invention is to provide a multi-location information gathering technique in which its primary instrumentation and the various information bearing locations are interconnected optically so as to make the technique especially suitable for gathering information located in hostile environments.

A further particular object of the present invention is to provide an uncomplicated, reliable and yet economical technique for obtaining from a given location or substantially simultaneously from a number of given locations information in the form of measurements of fluorescent light emanating from and characteristic of particular material at the information bearing locations and also a technique which utilizes a single fluorescence spectroscope even though more than one information bearing location may be involved and even though these locations may be in relatively hostile environments.

Still a further particular object of the present invention is to optically couple the fluorescent spectroscope just recited to the information bearing locations involved utilizing the long range optical giver technology developed by the communications industry.

Yet a further particular object of the present invention is to provide uncomplicated, reliable and yet economical light focusing and collecting devices for use in the technique last recited, while maintaining the normal signal gathering efficiency of fluorescence spectroscopy despite the severe optical constraints of interfacing to and transmitting the light through low attenuation fiber optic types.

As will be seen hereinafter, the overall information gathering technique disclosed herein is one which utilizes a single source of light provided at a location away from the information bearing location or locations. Means including an arrangement of optical fibers and the light source cooperate to direct individual beams of light into the various information bearing locations for causing the production of light signals which can be measured and which contain the information to be obtained at these latter locations. This "light signal" can be a result of fluoresence, light scattering, reflectance or other phenomena which causes light (both in the visible and invisible spectrum) to be re-emitted or produced as a result of the initiating beam. The optical means including its arrangement of fibers and coupling devices at the instrument as well as sampling devices at the distal end cooperate to direct outgoing beams of light towards locations to be measured, and return the remote signals to a central location, preferably the same location as the light source.

In the specific embodiments disclosed herein, the information to be obtained results from the fluorescence of specific material at each of the various information bearing locations. The incoming light beams, are used at least in part to cause the material to fluoresce and a single fluorescence spectroscope serves to detect and retrieve the information contained in the return beams produced as a result of the sample fluorescence at the remote end.

BRIEF DESCRIPTION OF THE DRAWINGS

The overall information gathering technique disclosed herein will be discussed in more detail hereinafter in conjunction with the drawing wherein:

FIG. 3B diagrammatically illustrates a beam splitter arrangement especially suitable for use in the system of FIG. 3A;

FIG. 3C diagrammatically illustrates another beam splitter arrangement suitable for use in the system of FIG. 3A;

FIG. 4A diagrammatically illustrates the optical characteristics at the end of an optical fiber of the general type used in the systems of FIGS. 1 and 3A;

FIG. 4B is an enlarged axial view, in section, illustrating an end segment of an optical fiber which may be used with the systems of FIGS. 1 and 3A and a light focusing and gathering device for use with such systems and designed in accordance with the second embodiment;

FIG. 4C is a view similar to FIG. 4B (and FIG. 2) but illustrating still another embodiment of a light focusing and gathering device particularly suitable for the system shown in FIG. 3A; and FIG. 5 is a diagrammatic illustration, in block diagram, of a system for obtaining fluorimetric information from one or a number of remote locations (substantially simultaneously) and in accordance with a preferred embodiment of the present invention.

DETAILED DESCRIPTION

Figure 1:
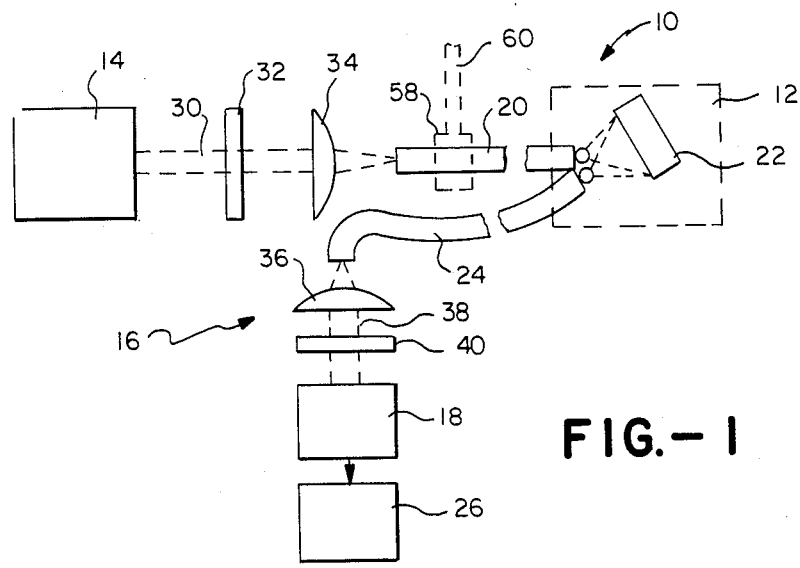
FIG. 1 diagrammatically illustrates a system for obtaining fluorimetric information from a single remote location in accordance with the present invention, using separate fibers for sending out the exciting light and receiving back the excited fluorescence, scattering, or reflectance signal.

Turning now to the drawing, attention is first directed to FIG. 1 which, as stated above, diagrammatically illustrates a system for obtaining specific fluorimetric information from a given location. The system is generally indicated at 10 and a particular information bearing location which may or may not be a hostile environment of the type recited above is indicated by dotted lines at 12. As will be discussed in more detail below, system 10 includes a source of light 14, which must be capable of being focused efficiently to the small diameter and acceptance angle of a low attenuation communication fiber, an overall optical network 16 including an arrangement of communication grade (low attenuation) optical fibers, and a fluorescent spectroscope 18. Light from source 14 is converted into a beam which by means of the arrangement of optical fibers, for example a single fiber 20, directs the light beam into location 12 and onto a section of material 22 for causing the latter to fluoresce in a way which is characteristic of the material. Network 16 including its arrangement of optical fibers, for example a single fiber 24 comprising part of the arrangement, collects part of the fluorescent signal into a returning beam of light containing the same information as the fluorescence to spectroscope 18. While not shown in FIG. 1, the source of light 14 and spectroscope 18 are preferably positioned at the same location. In addition, suitable data processing equipment 26 may be provided for acting on the information retrieved by the spectroscope 18 for subsequent processing purposes.

Referring now to the specific components making up overall system 10 in more detail, attention is first directed to light source 14. The light source may be of a suitable type which produces a beam of light 30 compatable with material 22 and fluorescent spectroscope 18, that is, a beam capable of causing material 22 to fluoresce in a way which is characteristic of the particular information to be sought from material 22. In a preferred embodiment, the light source is a laser apparatus and the beam 30 is monochromic light displaying a wavelength in the ultraviolet-visible-near infrared region.

The overall optical network 16 including its arrangement of optical fibers may be of any suitable type so long as it functions in the manner described above. In the embodiment illustrated in FIG. 1, this network includes an emission filter 32 and lens 34. The emission filter serves to eliminate laser cavity emission from the beam so as to confine the latter to a single wavelength. Lens 34 is appropriately located in beam 30 behind filter 32 and in front of one end of optical fiber 20 for focusing the beam onto the end of the optical fiber for transmission therethrough with minimum entry losses. The optical fiber itself is preferably one which is presently available in the communications industry for propagating a light beam, having a small cross-section, for example on the order of a few hundred microns, over many hundreds of yards with only slight attenuation. The specific optical fiber is one which can be readily purchased by designating it as the type used in the telephone system. Optical fiber 24 is preferably of the same type. In the embodiment illustrated, these two optical fibers form the entire arrangement of optical fibers comprising part of overall optical network 16. However, as will be discussed hereinafter, the optical fiber arrangement may be formed in a number of different ways.

Figure 2:
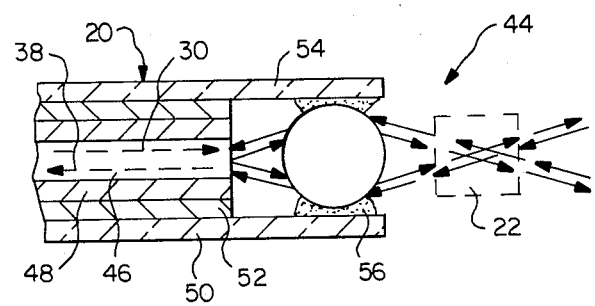
FIG. 2 is an enlarged axial sectional view illustrating one end section of an optical fiber which may be used with the system of the general type illustrated in FIG. 1 and a light focusing and gathering device designed for such a system.

In addition to emission filter 32, lens 34 and the two optical fibers just mentioned, overall optical network 16 includes a second lens 36, specifically a collector lens for capturing and straightening the outgoing beam generally indicated at 38, a wavelength filter 40 serving to filter out unwanted light from the beam. In addition to these components and those described above, overall optical network 16 includes suitable means cooperating with the end of optical fiber 20 at location 12 for focusing incoming beam 30 onto material 22 to produce fluorescence and suitable means cooperating with the adjacent end of optical fiber 24 for collecting light from the fluorescent display so as to form outgoing beam 38. Each of these latter means may be of any suitable type to be discussed below with respect to FIGS. 3A-3C. However, one such arrangement which can be used both as a focusing means and as a light collecting means is illustrated in FIG. 2 and generally designated by the reference numeral 44. As seen in this figure, arrangement 44 is in the form of a spherical lens, specifically a sapphire ball in a preferred embodiment. FIG. 2 also shows an end section of optical fiber 20 in detail. As seen there, this fiber includes a single light transmitting core at 46 concentrically disposed inside an outer cladding 48 which is bonded inside a glass tube 50 by means of suitable bonding cement located concentrically therebetween. The outermost glass tube includes an end section 54 which extends beyond the central core and cladding material for fixedly supporting lens 44 in a concentrically disposed position by suitable bonding cement generally indicated at 56. As a focusing device, lens 44 acts as a collector for incoming beam 30 (indicated by dotted lines) on one side and focuses the collection light to a point at material 22 on its opposite side. As a collector, the lens collects the light resulting from the fluorescent display on one side and focuses its collected light onto the end of the core 46 on its opposite side to provide outgoing beam 38 (indicated by dotted lines).

Overall information gathering system 10 has been described above as having two optical fibers, incoming fiber 20 and outgoing fiber 24. It is, however, preferable to provide an arrangement of optical fibers in which one fiber is common to both the incoming beam and the outgoing beam. For example, incoming beam 30 could be directed into location 12 in the same manner as described above. However, instead of utilizing a second, separate optical fiber 24 and associated collector lens, the optical fiber 20 and its associated focusing lens 44 could be used to collect the light from the fluorescent signal as will be discussed in more detail below with respect to FIGS. 3A–3C. This collected light could be directed back into and through optical fiber 20 toward source 14. However, a suitable beam splitter, for example those to be discussed specifically in FIGS. 3B and 3C (indicated by dotted lines at 58 in FIG. 1) would be provided or diverting this outgoing beam along a separate path defined by a separate optical fiber 60 which could otherwise be identical to previously recited optical fiber 24, but without a collector lens. The opposite end of this latter optical fiber would be coupled to lens 36 in the same manner as optical fiber 24. This overall configuration of course assumes that the outgoing beam of light is produced at a wavelength sufficiently different from the incoming beam so that the two can be separated.

Figure 3A:
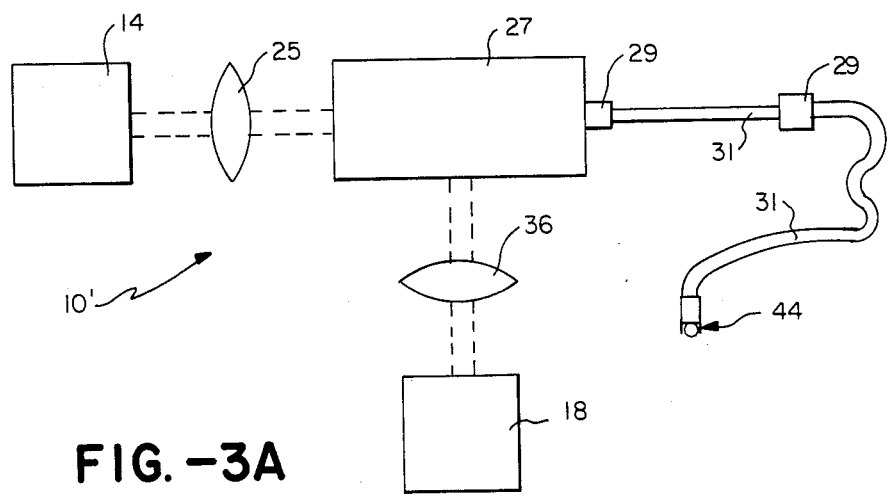
FIG. 3A diagrammatically illustrates a system similar to FIG. 1 but one which utilizes a common (single) optical fiber.

Having described system 10 and arrangement 44, attention is directed a modified system 10' which requires only a single fiber for directing the beam of light to a remote control location and for collecting the resultant light signal thereat, as briefly discussed above. This latter system is illustrated in FIG. 3A and includes a light source capable of focusing on a very small spot, e.g. the laser 14 illustrated in FIG. 1 or possibly an ultrahigh pressure mercury arc lamp such as used in fluorescence microscopy. A beam from this source is acted on by an illuminator lens 25 and thereafter passes onto a single fiber bidirectional coupler 27. A readily provided fiber optics connector 29 serves to connect one end of a long distance communication optics fiber 31 to the coupler. The fiber's other end is connected to another fiber 31 by a similar connector 29. The distal end of the second fiber 31 includes an arrangement 44 as discussed in FIG. 2 or like arrangement serving both to illuminate the sample under test and for collecting the light signal resulting therefrom. This light signal is returned by the fibers 31 to coupler 27 which redirects the collected light beam through the collector lens 36 and thereafter to the fluorescent spectrometer 18.

Two examples of couplers (which also serve as beam splitters) are illustrated in FIGS. 3B and 3C generally and are designated by the reference numerals 27' and 27", respectively. The beam splitter 27' cooperates with the previously recited illuminator lens 25, connector 27 and collector lens 36 along with a dichroic beam splitter or an intensity splitting beam splitter. The former must be changed for each set of fluorescence excitation and emission wavelengths used while the latter one does not but does impose a heavy penalty in signal levels. The arrangement 27" is a perforated mirror in order to geometrically separate the low convergence illumination beam (the incoming beam) and the more divergent return beam (which is limited only by the fiber numerical aperture).

Returning briefly to FIG. 2, attention is again directed to the combination beam focusing and collection arrangement 44. In describing this arrangement above, it was assumed that the material 22 being analyzed emits sufficient fluorescent light to provide a strong enough outgoing beam 38 to be analyzed. It was also assumed that there is a desire to collect all of the fluorescent light emitted by the material. In some cases, material 22 may not be of a type which by itself emits a strong enough fluorescent signal to be analyzed. In other cases, material 22 may include ingredients which fluoresce unwanted light. To eliminate these problems, lens 44 can be provided with an outer coating which combines with the incoming beam to cause the material 22 to give a fluorescent signal to a greater degree. For example, a solution of rubrene in polystyrene plastic coating could be provided when material 22 is iodine, which extinguishes the rubrene fluorescence. In any event, once material 22 is selected, the coating which will enhance fluorescence can be readily selected.

In order to more fully understand the way in which a single fiber can be used to direct a beam of light into a particular area under evaluation while at the same time serving to collect a resultant light signal therefrom and cause or aid in causing the production of a suitable light signal, attention is briefly directed to FIGS. 4A to 4C. FIG. 4A illustrates an optical fiber 20' similar to previously described fiber 20 but without the outer surface 50. Rather as seen in Figure 4A, fiber 20' includes a fiber core 46' and outer cladding 52' bonded together by suitable means 48'. FIG. 4A specifically illustrates the way in which the fiber 20' distributes and collects light without the aid of arrangements such as the arrangement 44 illustrated in FIG. 2. In FIG. 4A, the possible light which might result at the end of the fiber can be divided into three groups, the central cone shaped group designated at V1, the larger cone shaped area described at V2 and the area V3 outside the larger cone shaped area. All of the light emitted backwards towards the fiber core from within the volume V1 will be collected by the fiber. On the other hand, only part of the light emitted backwards towards the fiber core from within the volume V2 (excluding the volume V1) will be collected by the fiber. Finally, none of the light within the area designated at V3 will be collected by the fiber. The converse of each of these results is equally true, that is, light from the fiber will illuminate the entire volume V1, only part of the volume V2 and none of the volume V3.

An arrangement such as that illustrated in FIG. 4A is equivalent to a sample cell 0.22–0.8×fiber diameter (in depth), for practical values of the fiber numerical aperture. In order to increase the light signal, larger fiber core diameters could be used but soon become too costly and unwieldly, since the low attenuation communication fibers are rather small. Lenses can however be used to increase the apparent fiber diameter, but should be high in index to avoid strong performance alternations produced by sample refractive index changes.

A much more practical embodiment to use for directing a beam of light into a given area and for collecting the resultant light signal is the previously described arrangement 44 illustrated in FIG. 2. However, when the sample is not fluorescent, or when its fluorescence is not selective enough to derive exclusively from the species being sought, specific fluorescent reagents, fluorescense extinction reagents or extraction reagents can be used. These will create a fluoresce signal from the sample, or make the one they produce more selective. These reagents can easily be applied as a layer on top of the end face of the fiber core. The reagent must be a reversible one, in equilibrium with the sample medium, so that it does not get consumed and is yet able to reflect sample concentration fluctuations. It must also be stable and insoluable (or somehow chemically attached to the surface). For a lens system, the reagent location would have to be in and spaced in front of the lens, requiring a separate holder. To put it on the lens end face would be simpler, but to provide the focus there would require a lens index greater than two times the medium, which is extremely difficult given material limitations in the wavelength region discussed previously.

A different lens type, specifically the commercial selfor (Nippon Electric Company) rod lens, has a focus on its end surface, and can be used here to advantage. This lens is based on a rod with a parabolic radial distribution of refractive indices and a preselected length. Such a lens is illustrated in FIG. 4B at 44' in combination with the fiber 20" which is identical to previously illustrated fiber 20 and includes the same components including the same extended end. In this regard, note that the lens 44' is fixedly contained in the extension 54 in spaced relationship with he fiber core itself indicated at 46. In this way, the reagent can be located on the flat end surface of the rod lens.

The limited travel of the illumination beam in the sample before its spreading renders most of the generated fluorescence non-collectible by the fiber limits the methods total sensitivity. This can be avoided by containing the beam spread in a glass capillary as illustrated in FIG. 4C. There, the arrangement 44 is shown in combination with a glass capillary 80. Suitable means generally illustrated at 82 are provided for mechanically maintaining the capillary in concentric alignment with arrangement 44.

Having described overall information gathering system 10 in detail, it should be apparent that this system has been designed for obtaining specific fluorimetric information at only one location. Because of the relatively high cost of fluorimetric analytical equipment, specifically a fluorescence spectroscope and laser light sources, it would be highly desirable to use a single laser and spectroscope to obtain fluorimetric information from a number of different locations substantially simultaneously, that is, in sufficiently rapid succession to make it unnecessary to physically move the entire equipment to the various locations. The system for achieving this is illustrated in FIG. 5 and is generally indicated at 62. As seen there, the same laser 14 may be brought remotely to the various information bearing locations for producing previously recited beam 30. The same emission filter 32, lens 34 and beam splitter 58 described with respect to FIG. 1 can be provided for the same reasons described there.

As seen in FIG. 5, beam 30 is applied from the beam splitter to a cooperating end of an inlet optical fiber diagrammatically illustrated at 64. The inlet fiber may be identical in construction to previously described optical fiber 20. While not shown, the beam splitter itself includes an optical lens or like means for focusing beam 30 onto the adjacent end of fiber 64 whereby to assure that the entire beam enters the inlet fiber or the beam splitter may be like those shown in FIGS. 3B and 3C. The opposite end of this fiber is optically coupled, for example by means of a fiber connector and/or suitable lens, to the input of a star coupler 66. This latter device serves to alternatively direct beam 30 through a number of different outlets utilizing a combination of reflectors (e.g., mirrors) including at least one which is movable between a number of different positions. This movement can take place manually or automatic means can be readily provided. One such device is manufactured by Math Associates under the name of Two Part Optical Coupler. At each outlet of star coupler 66 is one end of a main or primary (long) optical fiber 68 which is coupled to its associated outlet by suitable optical means, for example a lens, so that beam 30 may be alternatively directed into any one of the longer fibers. Overall system 62 is shown including four primary fibers 68 in FIG. 3 and therefore star coupler 66 includes at least four outlets.

All of the components making up overall system 10 thus far described, that is, laser 14, emission filter 32, lens 34, beam splitter 58, inlet fiber 64, star coupler 66 and the coupled ends of primary fibers 68 are preferably located at the same central location. The various primary fibers extend from this location to the various information bearing locations. At each of these latter locations an outlet fiber 70 is optically coupled at one end to the adjacent end of an associated primary, fiber by suitable means, for example by an appropriate lens such that the beam 30 traveling through the primary fiber enters the outlet fiber. The other end of each outlet fiber includes what is referred to as an optrode for bringing its associated incoming beam 30 onto a corresponding material 22 and for collecting the light from the fluorescent display resulting therefrom. Outlet fibers 70 can be constructed in the same manner as previously described optical fibers 20 and the optrodes can be identical to and connected in the same manner as previously described focusing/collecting arrangement 44 or the other arrangements shown in FIG. 4.

The light collected by each optrode 44 in system 62 produces a corresponding outgoing beam 38, as in system 10. Each of these latter beams passes through outlet fiber 70 in the opposite direction as beam 30 and thereafter through its associated primary fiber 68, again in the opposite direction as beam 30. The various beams 38 are thereafter alternatively directed into star coupler 66 (through associated outlets of the latter) and from the star coupler into the single inlet fiber 64 towards beam splitter 58. After leaving inlet fiber 64 in the opposite direction as beam 30, beam 38 is directed through beam splitter 58 to a collector lens 36 which may be identical to the previously described collector lens comprising part of system 10. From the collector lens, the beam passes through a wavelength filter 40 and spatial filter 42 as in system 10 and, if desired, still another wavelength filter 40 and finally into spectroscope 18. The information from the spectroscope may be applied to appropriate data processing equipment 26 as in system 10.

From the foregoing, it should be apparent that a number of different remote locations which may or may not be in hostile environments can be substantially simultaneously monitored for fluorimetric information using a single laser and only one fluorescence spectroscope which are generally the most expensive components making up the overall system. In fact, in system 62, the only, duplication of components associated with the various information bearing locations are the primary fibers, outlet fibers and optrodes.

It should also be apparent that this multi-position technique is equally applicable for obtaining from various different locations information other than fluorimetric information. More specifically, a system similar to system 62 could be provided for monitoring temperature or other types of information which can be obtained optically, that is, by means of an incoming beam and an outgoing beam. For example, in the case of temperature, the incoming beam is passed into the area being monitored through an appropriate sensor such as the one described in U.S. Pat. No. 4,179,927. The outgoing beam is characteristic of the temperature at the sensor, as described in the patent just recited. In other words, the incoming beam in combination with the sensor would provide a signal in the sensor (e.g. the incoming beam itself) and this signal by means of reflection forms the basis for an outgoing beam directed back out of the sensor and towards its associated detector as described in U.S. Pat. No. 4,179,927. This is only one possible information gathering approach which could be used in lieu of or in combination with the gathering of fluorimetric information in overall system 62. In the case of temperature sensing or similar situations wherein the incoming and outgoing beams may have common wavelengths, it may in special cases be necessary to use separate optical networks for carrying the incoming and outgoing beams to reduce the background. However, the same laser and detector system could be readily provided as in system 62.

What is claimed is:

1. An optical fiber arrangements especially suitable for directing a beam of light into a given area adjacent a first location from a second location and/or for collecting newly generated fluorescent light emanating from a sample within said given area and directing it to said second location, said arrangement comprising: elongated optical fiber means having first and second opposite ends positioned at said first and second locations, respectively; a spherical lens having a focal point on each side thereof, whereby light at either one of said focal points is focused to the other by said lens; means for fixedly connecting said lens in confronting but spaced apart relationship with said first end of said optical fiber means such that one of the focal points of said lens is disposed at said first end and the other focal point is positionable within said given area, whereby light passing through said optical fiber means from its second end to its first end can be focused to a focusing point within said given area and light generated at said focusing point within said area can be focused into said first end of said fiber means for movement through latter to said second end; and means cooperating with said lens and designed to interact with said sample for altering the sample's fluorescent light emitting characteristics in a predetermined way.

2. An arrangement according to claim 1 herein said optical fiber means includes a single optical fiber.

3. An optical fiber arrangement especially suitable for directing a beam of light into a given area adjacent a first location from a second location and/or for collecting newly generated light within said given area and directing it to said second location, said arrangement comprising: elongated otpical fiber means having first and second opposite ends positioned at said first and second locations, respectively; a spherical lens having a focal point on each side thereof, whereby light at either one of said focal points is focused to the other by said lens; means for fixedly connecting said lens in confronting but spaced apart relationship with said first end of said optical fiber means such that one of the focal points of said lens is disposed at said first end and the other focal point is positionable within said given area, whereby light passing through said optical fiber means from its second end to its first end can be focused to a focusing point within said given area and light generated at said focusing point within said area can be focused into said first end of said fiber means for movement through the latter to said second end; and means defining a tubular glass capillary in optical alignment with said spherical lens opposite said first end of said fiber means.

4. An optical fiber arrangement especially suitable for directing a beam of light into a given area adjacent a first location from a second location and/or for collecting newly generated light within said given area and directing it to said second location, said arrangement comprising: elongated optical fiber means having first and second opposite ends positioned at said first and second locations, respectively; a spherical lens having a focal point on each side thereof, whereby light at either one of said focal points is focused to the other by said lens; means for fixedly connecting said lens in confronting but spaced apart relationship with said first end of said optical fiber means such that one of the focal points of said lens is disposed at said first end and the other focal point is positionable within said given area, whereby light passing through said optical fiber means from its second end to its first end can be focused to a focusing point within said given area and light generated at said focusing point within said area can be focused into said first end of said fiber means for movement through the latter to said second end; and an optical beam diverter which has an opening therethrough and which is located in confronting but spaced-apart relationship with said second end of said fiber means whereby to intercept light exiting said second end and directing it in a different path and a second lens located in confronting but spaced-apart relationship with said diverter, opposite said second end of said fiber means, for focusing light from a remote source through said diverter opening and into said second end for passage through said fiber means to said first end.

5. An optical fiber arrangement for use in a system for obtaining specific information form a particular sample substance of the type capable of interacting directly with a reversible, nonconsumable second substance when the latter is fluorescing such that as a result of said direct interaction, said second substance fluoresces in a way which is characteristic of said information, said arrangement comprising: optical fiber means having a light collecting end and including said second substance carried by said light collecting end; and means for causing said second substance to fluoresce at a location sufficiently close to said sample substance so as to provide said direct interaction and thereby cause said second substance to produce fluorescent light characteristics of said information.

6. An arrangement according to claim 5 wherein said sample substance is iodine and said second substance is rubrene.

7. An arrangement according to claim 5 wherein said optical fiber means includes an end surface serving as said end and wherein said second substance is chemically bonded to said end surface.

8. An optical fiber arrangement for use in a system for collecting fluorescent light containing specific information characteristic of a particular sample substance which is capable of fluorescing and for obtaining said specific information from said light, said arrangement comprising: means for causing said sample substance to fluoresce at a particular location; and means including a second substance for interacting with said sample substance to fluoresce at a particular location; and means including a second substance for interacting with said sample in a way which alters the sample's fluorescent light emanating characteristics in a predetermined way, whereby the altered light contains said specific information.

9. An arrangement according to claim 8 wherein said means including said second substance includes optical fiber means having end means serving as said light collecting means, 10. An arrangement according to claim 9, wherein said end means includes lens means serving as said light collecting means.

11. An arrangement according to claim 8 wherein said second substance interacts with said sample in a way which causes the latter to fluoresce to a greater extent than would be the case in the absence of said substance.

12. An arrangement according to claim 8 wherein said second substance interacts with said sample in a way which prevents certain fluorescent light from emanating from said sample.

13. An arrangement according to claim 8 wherein said second substance is from the group consisting of specific fluorescence producing regents, fluorescence extinction reagents and/or fluorescence extracting reagents.

14. An arrangement according to claim 13 wherein each of said reagents is a reversible one, in equilibrium with the sample and each reagent is stable so that it does not get lost or consumed.

15. An optical fiber arrangement for use in a system for obtaining specific information from a particular sample substance of the type capable of interacting directly with a reversible, nonconsumable second substance when the latter is fluorescing such that as a result of said direct interaction said second substance fluorescences in a way which is characteristic of said information, said arrangement comprising: optical fiber means having a light collecting end surface and said second substance bonded directly to said end surface of said optical fiber means; means for causing said second substance to fluoresce at a location in contact with said sample substance so as to provide said direct interaction and thereby cause said second substance to produce fluorescent light characteristic of said information and means including said optical fiber means for collecting some of said fluorescent light through said fiber means.

16. An arrangement according to claim 15 wherein said second substance is chemically bonded to said end surface.

17. An arrangement according to claim 16 wherein said optical fiber means includes a single optical fiber defining said light collecting end surface.

18. An arrangement for use in a system for obtaining specific information from a particular sample substance of the type capable of interacting directly with a reversible, nonconsumable second substance which itself is capable of fluorescing such that, as a result of said direct interaction, said second substance fluoresce in a way which is characteristic of said information, said arrangement comprising: means including a single optical fiber having a light collecting end surface and said second substance boned directly to said end surface; means for causing said second substance to fluoresce at a location sufficiently close to said sample substance so as to provide said direct interaction and thereby cause said second substance to produce fluorescent light characteristic of said information; and means including said single fiber for collecting some of said fluorescent light through said fiber.

19. An arrangement according to claim 18 wherein said second substance is chemically bonded to said light collecting end surfaces.

20. An arrangement for collecting fluorescent light containing specific information characteristic of a particular sample substance which is capable of fluorescing and for obtaining said specific information from said light, said system comprising: means for causing said sample substance to fluoresce at a particular location; optical fiber means having a light collecting end surface and a reversible, nonconsumable second substance bonded directly to said surface for interacting directly with said sample in a way which alters the sample's fluorescent light emanating characteristics in a predetermined way, whereby the altered light contains said specific information; and means including said fiber means for collecting some of said altered fluorescent light through said fiber means.

21. An arrangement according to claim 20 wherein said second substance is chemically bonded to said end surface.

22. An arrangement according to claim 21 wherein said optical fiber means includes a single fiber defining said light collecting end surface.

* * * * *